(12) United States Patent
Fulkerson et al.

(10) Patent No.: US 11,110,214 B2
(45) Date of Patent: Sep. 7, 2021

(54) METHODS AND SYSTEMS FOR MEASURING AND HEATING DIALYSATE

(71) Applicant: Fresenius Medical Care Holdings, Inc., Waltham, MA (US)

(72) Inventors: Barry Neil Fulkerson, Longmont, CO (US); Brian Thomas Kelly, Anaheim Hills, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 309 days.

(21) Appl. No.: 15/482,620

(22) Filed: Apr. 7, 2017

(65) Prior Publication Data

US 2018/0289879 A1 Oct. 11, 2018

(51) Int. Cl.
*A61M 1/16* (2006.01)
*A61M 1/26* (2006.01)

(52) U.S. Cl.
CPC .......... *A61M 1/166* (2014.02); *A61M 1/1656* (2013.01); *A61M 1/1668* (2014.02); *A61M 1/267* (2014.02); A61M 2202/064 (2013.01); A61M 2205/3317 (2013.01); A61M 2205/3375 (2013.01); A61M 2205/3393 (2013.01); A61M 2205/3569 (2013.01); A61M 2205/3653 (2013.01); A61M 2205/505 (2013.01)

(58) Field of Classification Search
CPC .. A61M 1/166; A61M 1/1656; A61M 1/1668; A61M 1/26; A61M 2202/064; A61M 2205/3317; A61M 2205/3375; A61M 2205/3393; A61M 2205/3569; A61M 2205/3653; A61M 2205/505
See application file for complete search history.

(56) References Cited

U.S. PATENT DOCUMENTS

| 3,242,456 A | 3/1966 | Duncan |
| 3,803,913 A | 4/1974 | Tracer |

(Continued)

FOREIGN PATENT DOCUMENTS

| EP | 0665026 A2 | 8/1995 |
| JP | 2002139165 A | 5/2002 |

(Continued)

OTHER PUBLICATIONS

International Search Report for PCT/US13/77234, dated Jun. 9, 2014.

(Continued)

*Primary Examiner* — Patrick Orme
(74) *Attorney, Agent, or Firm* — Novel IP (57) ABSTRACT

The present specification provides a dialysate management system for generating, weighing, and heating a dialysate fluid during a dialysis treatment. The dialysate management system includes a container and base enclosure. A bottom surface of the container rests within the base enclosure, which is configured to weigh the fluid in the container and measure its conductivity. The fluid may be heated using a heater integrated into the base enclosure or positioned in-line with a fluid pathway. The base of the container is preferably sloped and positioned within the internal volume of the container is a disposable prescription bag having a predefined quantity of prescription compositions that dissolve when water is poured into the container.

16 Claims, 7 Drawing Sheets

(56) References Cited

U.S. PATENT DOCUMENTS

| | | | |
|---|---|---|---|
| 3,961,918 A | 6/1976 | Johnson | |
| 3,989,625 A | 11/1976 | Mason | |
| 4,354,562 A | 10/1982 | Newman | |
| 4,397,519 A | 8/1983 | Cooney | |
| 4,403,765 A | 9/1983 | Fisher | |
| 4,430,098 A | 2/1984 | Bowman | |
| 4,480,483 A | 11/1984 | McShane | |
| 4,531,799 A | 7/1985 | Gray | |
| 4,535,637 A | 8/1985 | Feller | |
| 4,586,576 A | 5/1986 | Inoue | |
| 4,740,755 A | 4/1988 | Ogawa | |
| 4,828,543 A | 5/1989 | Weiss | |
| 5,000,274 A | 3/1991 | Bullivant | |
| 5,074,368 A | 12/1991 | Bullivant | |
| 5,114,580 A | 5/1992 | Ahmad | |
| 5,170,789 A | 12/1992 | Narayan | |
| 5,228,308 A | 7/1993 | Day | |
| 5,258,127 A | 11/1993 | Gsell | |
| 5,725,776 A | 3/1998 | Kenley | |
| 5,782,796 A | 7/1998 | Din | |
| 5,915,932 A | 6/1999 | Nabity | |
| 5,954,971 A | 9/1999 | Pages | |
| 5,989,438 A | 11/1999 | Fumiyama | |
| 6,044,691 A | 4/2000 | Kenley | |
| 6,045,097 A | 4/2000 | Gaffar | |
| 6,358,225 B1 | 3/2002 | Butterfield | |
| 6,487,904 B1 | 12/2002 | Myhre | |
| 6,491,656 B1 | 12/2002 | Morris | |
| 6,543,886 B1 * | 4/2003 | Hattori | B41J 2/17503 |
| | | | 347/85 |
| 6,638,478 B1 | 10/2003 | Treu | |
| 6,653,841 B1 | 11/2003 | Koerdt | |
| 6,681,624 B2 | 1/2004 | Furuki | |
| 6,691,047 B1 | 2/2004 | Fredericks | |
| 6,752,172 B2 | 6/2004 | Lauer | |
| 6,836,201 B1 | 12/2004 | Devenyi | |
| 6,948,697 B2 | 9/2005 | Herbert | |
| 7,087,026 B2 | 8/2006 | Callister | |
| 7,097,148 B2 | 8/2006 | DeWall | |
| 7,270,015 B1 | 9/2007 | Feller | |
| 7,387,022 B1 | 6/2008 | Korniyenko | |
| 8,040,493 B2 | 10/2011 | Fulkerson | |
| 8,105,487 B2 | 1/2012 | Fulkerson | |
| 8,114,288 B2 | 2/2012 | Robinson | |
| 8,137,553 B2 | 3/2012 | Fulkerson | |
| 8,240,636 B2 | 8/2012 | Smith | |
| 8,395,761 B2 | 3/2013 | Fulkerson | |
| 8,475,399 B2 | 7/2013 | Fulkerson | |
| 8,535,522 B2 | 9/2013 | Fulkerson | |
| 8,597,505 B2 | 12/2013 | Fulkerson | |
| 8,771,511 B2 | 7/2014 | Robinson | |
| 9,157,786 B2 | 10/2015 | Fulkerson | |
| 9,199,022 B2 | 12/2015 | Fulkerson | |
| 9,201,036 B2 | 12/2015 | Fulkerson | |
| 9,295,772 B2 | 3/2016 | Fulkerson | |
| 9,308,307 B2 | 4/2016 | Fulkerson | |
| 9,352,282 B2 | 5/2016 | Fulkerson | |
| 9,354,640 B2 | 5/2016 | Byler | |
| 9,358,331 B2 | 6/2016 | Fulkerson | |
| 9,360,129 B2 | 6/2016 | Smith | |
| 9,415,152 B2 | 8/2016 | Robinson | |
| 9,517,296 B2 | 12/2016 | Fulkerson | |
| 9,759,710 B2 | 9/2017 | Fulkerson | |
| 2002/0151804 A1 | 10/2002 | O'Mahony | |
| 2002/0158019 A1 | 10/2002 | Collins | |
| 2003/0048185 A1 | 3/2003 | Citrenbaum | |
| 2003/0056585 A1 | 3/2003 | Furuki | |
| 2003/0220598 A1 | 11/2003 | Busby | |
| 2004/0031756 A1 | 2/2004 | Suzuki | |
| 2005/0086008 A1 | 4/2005 | Digianfilippo | |
| 2005/0101901 A1 | 5/2005 | Gura | |
| 2005/0131332 A1 | 6/2005 | Kelly | |
| 2005/0133439 A1 | 6/2005 | Blickhan | |
| 2006/0195064 A1 | 8/2006 | Plahey | |
| 2006/0226057 A1 | 10/2006 | Robinson | |
| 2006/0289342 A1 | 12/2006 | Sugioka | |
| 2007/0007208 A1 * | 1/2007 | Brugger | A61M 1/1656 |
| | | | 210/645 |
| 2007/0112297 A1 | 5/2007 | Plahey | |
| 2007/0179425 A1 | 8/2007 | Gura | |
| 2007/0253463 A1 | 11/2007 | Perry | |
| 2007/0269340 A1 | 11/2007 | Dannenmaier | |
| 2008/0021377 A1 * | 1/2008 | Kienman | A61M 1/1696 |
| | | | 604/29 |
| 2008/0041792 A1 | 2/2008 | Crnkovich | |
| 2008/0214979 A1 | 9/2008 | Brugger | |
| 2008/0230450 A1 | 9/2008 | Burbank | |
| 2008/0258735 A1 | 10/2008 | Quackenbush | |
| 2008/0290974 A1 | 11/2008 | Adams | |
| 2009/0008306 A1 | 1/2009 | Cicchello | |
| 2009/0101549 A1 | 4/2009 | Kamen | |
| 2009/0101552 A1 | 4/2009 | Fulkerson | |
| 2009/0101577 A1 | 4/2009 | Fulkerson | |
| 2009/0127193 A1 | 5/2009 | Updyke | |
| 2010/0129247 A1 | 5/2010 | Lauer | |
| 2010/0140149 A1 | 6/2010 | Fulkerson | |
| 2010/0331754 A1 | 12/2010 | Fulkerson | |
| 2011/0054378 A1 | 3/2011 | Fulkerson | |
| 2011/0071465 A1 | 3/2011 | Wang | |
| 2011/0120946 A1 * | 5/2011 | Levin | A61M 1/1666 |
| | | | 210/637 |
| 2011/0160649 A1 * | 6/2011 | Pan | A61M 1/28 |
| | | | 604/28 |
| 2011/0185722 A1 * | 8/2011 | Sebesta | A61M 1/14 |
| | | | 60/527 |
| 2011/0303598 A1 | 12/2011 | Lo | |
| 2011/0315611 A1 * | 12/2011 | Fulkerson | A61M 1/3639 |
| | | | 210/96.2 |
| 2012/0199205 A1 | 8/2012 | Eyrard | |
| 2012/0214117 A1 | 8/2012 | Broker | |
| 2012/0310150 A1 * | 12/2012 | Brandl | A61J 1/2093 |
| | | | 604/29 |
| 2013/0165847 A1 | 6/2013 | Scarpaci | |
| 2013/0220907 A1 | 8/2013 | Fulkerson | |
| 2013/0280104 A1 | 10/2013 | Heide | |
| 2014/0188040 A1 | 7/2014 | Busby | |
| 2014/0276537 A1 | 9/2014 | Kruse | |
| 2015/0258263 A1 | 9/2015 | Hogard | |
| 2015/0314055 A1 | 11/2015 | Hogard | |
| 2016/0069732 A1 | 3/2016 | Fulkerson | |
| 2016/0109398 A1 | 4/2016 | Fulkerson | |
| 2016/0317733 A1 | 11/2016 | Fulkerson | |
| 2016/0319954 A1 | 11/2016 | Smith | |
| 2017/0007756 A1 | 1/2017 | Robinson | |
| 2017/0021085 A1 | 1/2017 | Fulkerson | |
| 2017/0021088 A1 | 1/2017 | Fulkerson | |
| 2017/0021306 A1 | 1/2017 | Fulkerson | |
| 2017/0023953 A1 | 1/2017 | Byler | |
| 2017/0232177 A1 | 8/2017 | Fulkerson | |

FOREIGN PATENT DOCUMENTS

| | | |
|---|---|---|
| WO | 20015069412 A1 | 7/2001 |
| WO | 2009073567 | 6/2009 |
| WO | 2010042666 | 4/2010 |
| WO | 2010062698 | 6/2010 |
| WO | 2010081121 | 7/2010 |
| WO | 2012108910 | 8/2012 |
| WO | 2014105267 A1 | 7/2014 |
| WO | M14105755 | 7/2014 |
| WO | 2014161008 | 10/2014 |
| WO | 2017106356 A1 | 6/2017 |

OTHER PUBLICATIONS

International Search Report for PCT/US2013/068506, dated Apr. 9, 2014.

International Search Report for PCT/US14/60122, dated Jan. 21, 2015.

International Preliminary Report on Patentability for PCT/US13/77234, dated Jun. 30, 2015.

(56) References Cited

OTHER PUBLICATIONS

International Search Report for PCT/US16/66671, dated Apr. 20, 2017.
International Search Report for PCT/US14/35051, dated Sep. 5, 2014.
International Search Report for PCT/US09/31228, dated Jun. 19, 2009.
International Search Report for PCT/US17/21389, dated Jun. 15, 2017.
International Search Report for PCT/US17/21456, dated Jun. 21, 2017.
International Search Report PCT/US08/85062, dated Mar. 20, 2009, XCorporeal, Inc.
International Search Report for PCT/US10/20698, Xcorporeal, Inc., dated Jun. 16, 2010.
International Search Report for PCT/US09/59906, Xcorporeal, Inc., dated May 8, 2012.
International Search Report for PCT/US09/62840, Xcorporeal, Inc. dated Feb. 10, 2012.
International Search Report for PCT/US11/53184, Xcorporeal, Inc., dated Mar. 2, 2012.
International Search Report for PCT/US09/59907, Xcorporeal, Inc., dated Apr. 13, 2010.
International Search Report for PCT/US10/29500, Xcorporeal, Inc., dated Jul. 2, 2010.
International Search Report for PCT/US18/25328, dated Jun. 20, 2018.

\* cited by examiner

METHODS AND SYSTEMS FOR MEASURING AND HEATING DIALYSATE

CROSS-REFERENCE TO RELATED APPLICATIONS

The present application relates to the following applications, all of which are herein incorporated by reference in their entirety:

U.S. patent application Ser. No. 15/447,519, entitled "Split Reservoir Bags and Method of Using Split Reservoir Bags to Improve the Heating and Generation of Dialysate" and filed on Mar. 2, 2017.

U.S. patent application Ser. No. 14/924,134, entitled "Method and System of Monitoring Electrolyte Levels and Composition Using Capacitance or Induction" and filed on Oct. 27, 2015, which is a continuation application of U.S. patent application Ser. No. 13/725,178, of the same title, filed on Dec. 21, 2012, and issued as U.S. Pat. No. 9,201,036 on Dec. 1, 2015. U.S. patent application Ser. No. 14/848,012, entitled "Load Suspension and Weighing System for a Dialysis Machine Reservoir" and filed on Sep. 8, 2015, which is a continuation application of U.S. patent application Ser. No. 13/726,450, of the same title, filed on Dec. 24, 2012, and issued as U.S. Pat. No. 9,157,786 on Oct. 13, 2015.

U.S. patent application Ser. No. 15/055,857, entitled "Manifold Diaphragms" and filed on Feb. 29, 2016, which is a continuation application of U.S. patent application Ser. No. 13/852,918, of the same title, filed on Mar. 28, 2013, and issued as U.S. Pat. No. 9,308,307 on Apr. 12, 2016, which is a continuation-in-part application of U.S. patent application Ser. No. 13/023,490, entitled "Portable Dialysis Machine", filed on Feb. 8, 2011, and issued as U.S. Pat. No. 8,597,505 on Dec. 3, 2013;

U.S. patent application Ser. No. 15/147,639, entitled "Portable Dialysis Machine with Improved Reservoir Heating System" and filed on May 5, 2016, which is a continuation application of U.S. patent application Ser. No. 13/726,457, of the same title, filed on Dec. 24, 2012, and issued as U.S. Pat. No. 9,358,331 on Jun. 7, 2016, which is a continuation-in-part application of U.S. patent application Ser. No. 13/023,490, entitled "Portable Dialysis Machine", filed on Feb. 8, 2011, and issued as U.S. Pat. No. 8,597,505 on Dec. 3, 2013; U.S. patent application Ser. No. 15/341,953, entitled "Portable Dialysis Machine" and filed on Nov. 2, 2016, which is a continuation application of U.S. patent application Ser. No. 14/040,362, of the same title, filed on Sep. 27, 2013, and issued as U.S. Pat. No. 9,517,296 on Dec. 13, 2016, which is a continuation application of U.S. patent application Ser. No. 13/023,490, of the same title, filed on Feb. 8, 2011, and issued as U.S. Pat. No. 8,597,505 on Dec. 3, 2013.

FIELD

The present specification is directed to dialysis systems with improved structural and functional features. In particular, the present specification is directed to a dialysate management system for holding, heating and measuring dialysate.

BACKGROUND

Blood purification systems, which are used for conducting hemodialysis, hemodiafiltration or hemofiltration, involve the extracorporeal circulation of blood through an exchanger with a semi-permeable membrane. Such systems further include fluid circuits for circulating blood, replacement fluid, and/or dialysate including certain electrolytes in concentrations approximating the blood of a healthy person.

Hemodialysis ("HD"), using a high flux membrane, removes toxins from the blood using transport mechanisms including diffusion and ultrafiltration (i.e., convective transport). Diffusion removes toxins using a concentration gradient across the semi-permeable membrane. For example, in a hemodialysis circuit, the dialysate solution flows on one side of the dialyzer membrane in one direction while simultaneously blood flows on the other side of the membrane. Ultrafiltration occurs when water (along with small solutes) is driven from the blood to dialysate in the dialyzer because of the hydrostatic pressure gradient between the blood and dialysate compartments (i.e., the transmembrane pressure ("TMP")).

Conventionally, a reservoir bag is provided for storing the dialysate. The dialysate, which is typically made of filtered water mixed with certain prescribed compositions, is heated to a predefined temperature, namely the patient's body temperature, before being implemented in a hemodialysis treatment. For example, a clinician may take a 10-liter jug, fill it with 6 liters of water, mix in powdered forms of the prescribed compositions, and then shake the combination to mix the water and compositions. A sample of the mixture is then taken extracted from the bag and subjected to a conductivity and/or concentration measurement, which is inputted into the dialysis machine. The bag is connected to the dialysate circuit of the dialysis system and the dialysate solution is then pumped through a sorbent cartridge to filter it. Once passed through the sorbent, the filtered dialysate passes into a reservoir where it is subsequently heated.

There are several disadvantages with this conventional system. First, in a standard dialysis treatment, it takes too long to generate filtered, heated dialysate. The priming time requires first waiting for all of the dialysate mixture to pass through a sorbent cartridge and then waiting for all of the filtered dialysate to heat to a predefined temperature, e.g. 37° C. This serial approach to creating filtered, heated dialysate unnecessarily extends patient treatment times and increases patient discomfort.

Second, in conventional systems, operators often forget where they are in the dialysate generation process. Consequently, many lose track as to whether they filled the reservoir with the right amount of water, added in each one of the required compositions, and/or added in the right amount of each composition. As a result, dialysis treatments often have to be restarted in order to ensure the right dialysate mixture is being used.

Hence, there is need for a dialysate management system, and accompanying methods of use, which enable filtered, heated dialysate to be generated without having to serially filter and then heat the dialysate. There is also need for a dialysate container that is physically separate and distinct from the dialysis system and that is configured to determine the conductivity and weight of any solution contained therein, thereby allowing for the elimination of weight measurement and/or conductivity elements from the dialysis machine. There is also a need for dialysate containers, and accompanying methods of use, which reduce the overall number of steps in a conventional dialysis treatment and, hence, also reduce the time required in preparing a dialysis system for performing dialysis.

SUMMARY

In some implementations, the present specification discloses a dialysate generation system for generating a dialysate fluid during a dialysis treatment, comprising: a container configured to hold fluid, wherein the container comprises an internal base surface that, relative to a substantially horizontal surface, has a slope in a range of 0.1 degrees to 50 degrees and an outlet tube that is in fluidic communication with a fluid circuit of a dialysis system; and a base enclosure configured to detachably receive a bottom portion of the container, wherein said base enclosure comprises: a first scale in physical communication with the bottom portion of the container and configured to weigh the fluid positioned within the container; and a conductivity sensor positioned proximate the bottom portion of the container and configured to measure a conductivity of the fluid in the container.

Optionally, the container further comprises powdered compositions enclosed within a disposable porous material.

Optionally, the outlet tube is positioned proximate to a lowest point of said sloped internal base surface and opposite from the highest point of said sloped internal base surface.

Optionally, said outlet tube is positioned at a height ranging from ¼ to ½ inch from an external bottom surface of said container.

Optionally, the dialysate generation system further comprises a wireless transmitter configured to wirelessly transmit at least one of weight data and conductivity data to a controller in a dialysis machine, wherein said dialysis machine is in electronic communication with said dialysate generation system.

Optionally, the first scale comprises a flexure assembly. Optionally, the flexure assembly comprises at least one of a load cell or strain gauge.

Optionally, the conductivity sensor comprises a conductivity coil.

Optionally, the conductivity sensor comprises ultrasonic sensors.

Optionally, the base enclosure and container are physically separate from the dialysis system and wherein the container and base lack a heating element.

In some implementations, the present specification describes a dialysis system, comprising: a dialysis machine comprising: a dialysate fluid circuit having a fluid pathway and a blood fluid circuit, a dialyzer in fluid communication with the dialysate fluid circuit and blood fluid circuit, a sorbent cartridge in fluid communication with said dialysate fluid circuit, a plurality of pumps in physical communication with the dialysate fluid circuit and the blood fluid circuit, a processing unit for controlling an operation of the plurality of pumps, and a heating element configured to heat fluid as it flows through the fluid pathway; and a dialysate generation system physically separate from said controller unit, the dialysate generation system comprising: a container configured to hold fluid, wherein the container comprises an outlet tube that is in fluid communication with said fluid pathway in the dialysate fluid circuit, a bottom portion, and an internal base surface, and a base enclosure configured to detachably receive the bottom portion of the container, wherein said base enclosure comprises: a scale in physical communication with the bottom portion of the container and configured to weigh the fluid positioned within the container; and a conductivity sensor configured to measure a conductivity of the fluid in the container.

Optionally, the heating element is a resistive heating element positioned longitudinally along and cylindrically around said fluid pathway.

Optionally, the heating element is an inductive heating element positioned longitudinally along and cylindrically around said fluid pathway.

Optionally, the container comprises an internal base surface that, relative to a substantially horizontal surface, has a slope in a range of 0.1 degrees to 50 degrees.

Optionally, the outlet tube is positioned proximate to a lowest point of said sloped internal base surface and opposite from the highest point of said sloped internal base surface.

Optionally, the outlet tube is positioned at a height ranging from ¼ to ½ inch from an external bottom surface of said container.

Optionally, the container further comprises powdered compositions enclosed within a disposable porous material.

Optionally, the dialysate generation system further comprises a wireless transmitter configured to wirelessly transmit at least one of weight data and conductivity data to the processing unit.

In some implementations, the present specification discloses a method of generating dialysate using a dialysate generation system, wherein said dialysate generation system is physically separate from a dialysis controller unit and wherein said dialysate generation system comprises a container configured to hold fluid, wherein the container comprises an internal base surface and an outlet tube that is in fluid communication with a fluid pathway positioned in the dialysis controller unit and a base enclosure configured to detachably receive a bottom portion of the container, wherein said base enclosure comprises: a scale in physical communication with the bottom portion of the container and configured to weigh the fluid positioned within the container and a conductivity sensor positioned proximate the bottom portion of the container and configured to measure a conductivity of the fluid in the container, the method comprising: filling a predefined quantity of water into the container; placing the container in the base enclosure; adding at least one powdered composition to the water in the container to create dialysate fluid; weighing the dialysate fluid in the container using said scale; measuring a conductivity of the dialysate fluid in the container using said conductivity sensor; determining if the weight and conductivity of the fluid in the container falls within a range of acceptable values for weight and conductivity; causing the dialysate fluid to flow from the outlet tube to the fluid pathway positioned in the dialysis controller unit; heating the dialysate fluid in the fluid pathway using an in-line heating element; and passing the dialysate fluid over a sorbent for filtration.

Optionally, the in-line heating element is a resistive heating element positioned longitudinally along and cylindrically around said fluid pathway.

Optionally, the in-line heating element is an inductive heating element positioned longitudinally along and cylindrically around said fluid pathway.

Optionally, the container comprises an internal base surface that, relative to a substantially horizontal surface, has a slope in a range of 0.1 degrees to 50 degrees.

Optionally, the method further comprises adjusting a measured weight of the dialysate fluid to account for an unequal distribution of dialysate fluid across the internal base surface due to said slope in a range of 0.1 degrees to 50 degrees.

In some implementations, the present specification discloses a dialysate generation system for generating a dialysate fluid during a dialysis treatment, comprising: a dialysis machine comprising a fluid circuit; a container configured to receive fluid from the fluid circuit, the container comprising: an outlet fluidically connected to the fluid circuit, and a bottom portion having a sloped internal surface having a slope of 0.1 degrees to 50 degrees; and a base configured to detachably connect to the bottom portion, the base comprising: a scale configured to weigh the container and fluid from the fluid circuit, and a conductivity sensor positioned proximate the bottom portion and configured to measure a conductivity of the fluid from the fluid circuit.

The aforementioned and other implementations of the present specification shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

While the present specification discloses inventions that are embodied in many different forms, for the purpose of promoting an understanding of the principles of the specification, reference will now be made to the embodiments illustrated in the drawings and specific language will be used to describe the same. Any alterations and further modifications in the described embodiments, and any further applications of the principles of the specification as described herein are contemplated and incorporated herein, as would normally occur to one skilled in the art to which the specification relates.

The term "and/or" means one or all of the listed elements or a combination of any two or more of the listed elements.

The terms "comprises" and variations thereof do not have a limiting meaning where these terms appear in the description and claims.

Unless otherwise specified, "a", "an", "the", "one or more", and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present specification is directed towards multiple implementations. The following disclosure is provided to enable a person having ordinary skill in the art to practice the invention. Language used in this specification should not be interpreted as a general disavowal of any one specific implementation or used to limit the claims beyond the meaning of the terms used therein. The general principles defined herein may be applied to other implementations and applications without departing from the spirit and scope of the invention. Also, the terminology and phraseology used is for the purpose of describing exemplary implementations and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific implementation may be used and combined with any other implementation unless clearly indicated otherwise.

In an implementation, the present specification provides a dialysate management system or dialysate generation system that includes a dialysate container with a base enclosure, detached and separate from the dialysis system, which is configured to weigh any solution placed in the container, measure the conductivity of the solution in the container and, optionally, heat the solution or direct the solution through an in-line heating element. In one implementation, the dialysate management system is used in conjunction with a dialysis system and is connected via a wireless or wired interface to the controller, base unit and/or pump unit of the dialysis system. It should be noted herein that the terms dialysate management system and dialysate generation system may be used interchangeably.

In implementations, a pre-defined quantity of water is filled in the dialysate container and a pre-defined amount of prescription powder is mixed therein. In an implementation, a disposable liner or a disposable flexible container is fitted within the container for holding the prescription powder which eventually dissolves in the water filled in the container.

The present specification provides a dialysate management system which can rapidly heat dialysate without having to first transfer the dialysate to a reservoir bag which is typically heated within a dialysis machine. The dialysate management system includes a container configured to be placed on a portable base, holder, cozy, or other partial enclosure having a means to determine the conductivity and/or weight of the solution contained in the container, thereby eliminating the need for a dialysis machine used in conjunction with the container to comprise integrated heating and conductivity measurement elements and effectively reducing the weight of the dialysis machine. The dialysate container of the present specification reduces the number of steps and the time required in preparing a dialysis system for performing dialysis.

Figure 1:
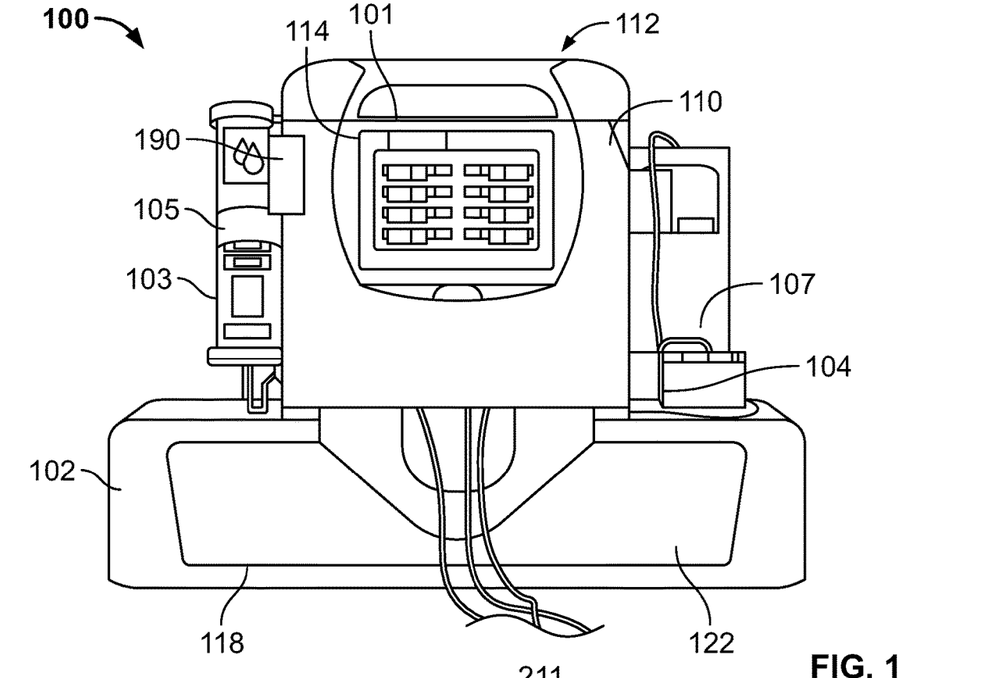
FIG. 1 is a front view of an exemplary dialysis system.
Figure 2:
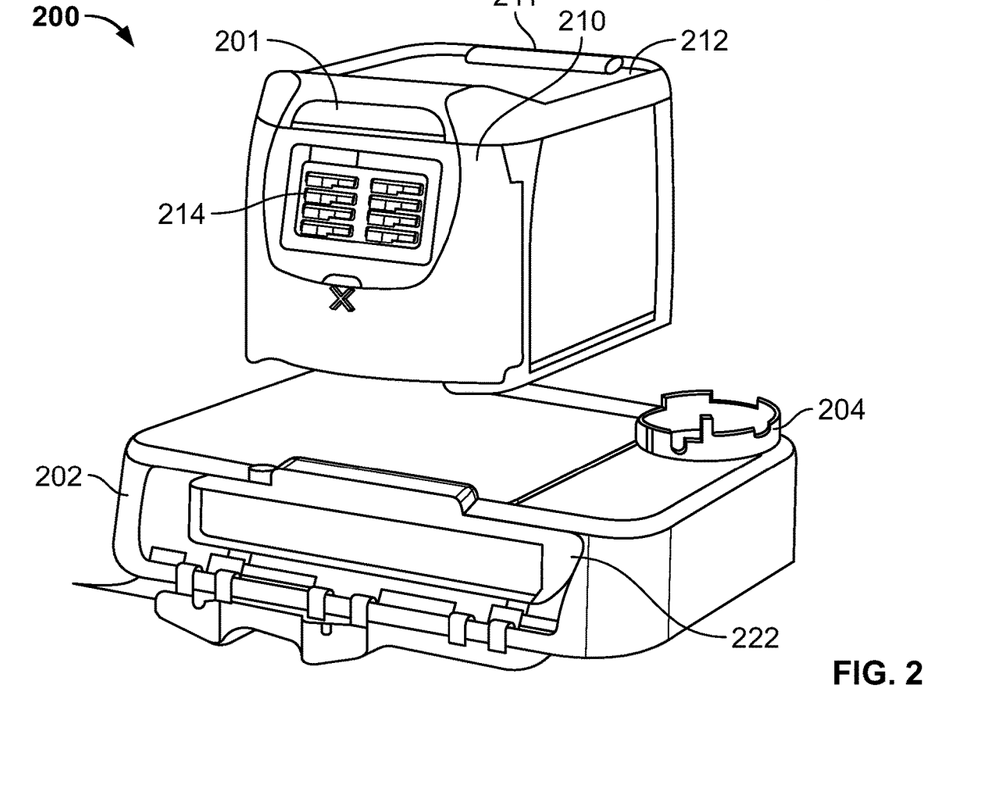
FIG. 2 is a perspective view of the exemplary dialysis system of FIG. 1.

FIGS. 1 and 2 illustrate front and perspective views respectively, of a dialysis system 100, 200 with which the dialysate management systems of the present specification may be used. It should be apparent to those of skill in the art that the dialysis system 100, 200 shown in FIGS. 1 and 2 is merely exemplary and that the dialysate management system of the present specification may be used with any type of dialysis system comprising a sorbent system, with or without an integrated reservoir system.

Referring to FIGS. 1 and 2 concurrently, the dialysis system 100, 200 comprises a top unit 101, 201 that is optionally connected to a bottom unit or base unit 102, 202. The bottom unit 102, 202 comprises a reservoir 122, 222 for fluid storage, measurement, and monitoring. The top unit 101, 201, also referred to as the main unit or controller unit, comprises a graphical user interface 114, 214, a plurality of pumps, a processing unit for controlling the operating of the plurality of pumps, electronics, and a door 110, 210 with a power lock and mechanical backup mechanism.

In implementations, the top unit also provides electronic interfaces, such as Ethernet connections or USB ports, to enable a direct connection to a network, thereby facilitating remote prescription verification, compliance vigilance, and other remote servicing operations. In addition, the electronic interfaces are used to transmit, either wired or wirelessly, the measured values of weight, conductivity, and temperature to the dialysis machine, which verifies the values and sends the confirmation back to the dialysate management system, as described in greater detail below. The interfaces are electronically isolated, thereby ensuring patient safety regardless of the quality of the interfacing device.

In implementations, the graphical user interface 114, 214 provides for a simple user interface with the dialysis system 100, and includes maximal use of colors and a touch screen. The touch screen allows multiple user input configurations, provides multiple language capability, and can be readily seen at night (particularly with brightness controls and night-vision colors).

The top unit 101, 201 further comprises handles 211 and a workspace in the form of a useable shelf 112, 212, also located at the top. The handles 211, located on the upper pumping portion of the system, are directly connected to the internal structure or frame of the system and are not simply an extension of the exterior plastic molding, housing, or skins surrounding the top unit 101, 201. The direct connection to the internal frame of the system permits using the handle to reposition the system in a manner that is safe and can reliably handle the load, particularly when the instrument is in operation with six liters of water (adding approximately 40 lbs). The bottom unit 102, 202 has a door 118 which, when opened or pulled out and not blocked by any protrusion, slides the reservoir 122 out, or otherwise makes the reservoir 122 accessible to a user, to allow a user to insert or change fluids used for dialysis.

A clasp 105 is used to detachably affix a dialyzer 103 to a first side of the top unit 101, 201. A sorbent cartridge locking base 104, 204 used to detachably affix a sorbent cartridge 107 to a second, opposing side of the top unit 101, 201. It should be appreciated that in other implementations, the clasp, hemofilter, sorbent cartridge locking base, and sorbent cartridge can be positioned on the same side of the top unit. In either case, the bottom unit 102, 202 has a sufficiently larger area relative to the top unit 101, 201 such that shelves are formed on either side of the top unit 101, 201 to hold the sorbent cartridge, to hold an infusate jar, to capture any spillage, and/or to channel any leaks into a leak detector.

Optionally, in an implementation, as shown in FIG. 1, between the dialyzer 103 and door 110 are anti-coagulant pumps in the form of syringe pumps 190. The use of the anti-coagulant syringe pump is optional. Optionally, the top unit 101, 201 can comprise a bottle holder that has a spiked base to receive a bottle, top-down, within the bottle holder housing. Infusion lines are connected to the inlet of the blood pump, outlet of the blood pump, or outlet of the dialyzer (blood side). The infusion lines could also 'thread' through air bubble detectors to sense if/when the anti-coagulant is emptied or blocked.

In an implementation, the reservoir 122, 222 may be eliminated in favor of a dialysate management system that is remotely positioned relative to, and not physically attached to, the top unit 101, 201. In this case, the dialysate management system is separate from, and is not physically connected to, the dialysis machine, but rather fluidically connected, thereby allowing it to be in a separate physical location from the dialysis machine, such as on the floor.

In conventional dialysis systems, the dialysate is pumped out from a container, such as a jug, and, after being subject to a priming process, is transferred into the reservoir 122, 222. The dialysate management system described in the present specification eliminates the need for a discrete reservoir integrated into the dialysis system, thereby enabling greater portability of the dialysis system.

In implementations, the top unit 101, 201 of the dialysis system 100, 200 comprises a blood fluid path or circuit and a dialysate fluid paths or circuit, wherein the dialysate fluid circuit and blood fluid circuit are in fluid communication with the dialyzer and wherein the sorbent cartridge is in fluid communication with the dialysate fluid circuit. The patient's toxin-containing blood is pumped from a blood vessel of the patient and is circulated, using a blood pump, in the blood circuit on one side of the membrane (dialyzer/dialyzer cartridge) and the dialysate, comprising the main electrolytes of the blood in concentrations prescribed by a physician, is circulated on the other side in the dialysate circuit. The circulation of dialysate fluid thus provides for the regulation and adjustment of the electrolytic concentration in blood.

The dialyzer cartridge used may be of any type suitable for hemodialysis, hemodiafiltration, hemofiltration, or hemoconcentration, as are known in the art. Used dialysate fluid from the dialyzer enters the dialysate circuit. In an implementation, a dialysate pump draws spent dialysate from the dialyzer cartridge and forces the dialysate into a dialysate regeneration system and back into the dialyzer cartridge in a multiple pass loop, thus generating "regenerated" or fresh dialysate. Thus, a sorbent cartridge is provided in the dialysate circuit, which enables regeneration of fresh dialysate from the spent dialysate coming from the dialyzer. By regenerating the dialysate with sorbent cartridges, the dialysis system requires only a small fraction of the amount of dialysate of a conventional single-pass hemodialysis device.

A heater is also provided to maintain the temperature of dialysate fluid in the container at the required level. The temperature of the dialysate fluid can be sensed by a temperature sensor located just before the fluid's entry into the dialyzer.

Figure 3A:
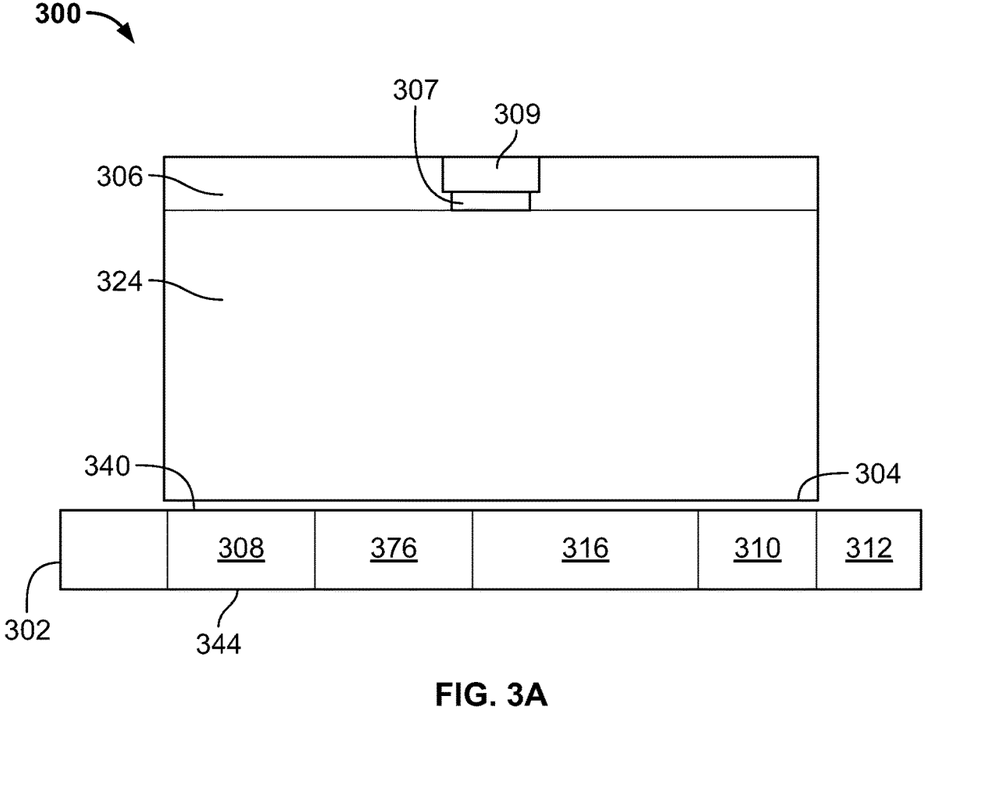
FIG. 3A illustrates an exemplary block diagram of a dialysate management system, in accordance with an implementation of the present specification.

FIG. 3A illustrates an exemplary block diagram of a dialysate management system in accordance with an embodiment of the present specification. Each component in the dialysate management system 300 may be fabricated from any medical grade resilient material such as stainless steel, polyethylene, polypropylene, polystyrene, PLA or other polymers. The dialysate management system comprises a container 324 and a base into which the container 324 is detachably positioned.

In an implementation, the container 324 is fabricated from molded plastic and is rectangular. In other implementations, the container 324 may be designed to have any suitable shape, including polygonal and cylindrical. In an implementation, the container 324 also comprises a handle and a spout. In various implementations, the dimensions of the container 324 are in a range of approximately 10 to 14 inches high×7.25 to 11.25 inches wide×5.63 to 9.63 inches deep and the weight of the container 324 is in a range of approximately 15 to 25 pounds. In a preferred embodiment, the dimensions of the container 324 are 12 inches high×9.25 inches wide×7.63 inches deep and the container 324 weighs less than 20 pounds, thereby being easier to lift and enabling the portability of the dialysis system. In various implementations, the container 324 has a capacity of approximately 2 to 4 gallons, or approximately 7.5 to 15 L. More specifically, when the dialysis system initiates operation, the container 324 holds at least 6 L of water. After treatment, the container 324 may hold up to 10 L of fluid, some of which has been removed from the patient. Therefore, the capacity of the container 324 is preferably in a range of 12 L to 15 L.

In an implementation, the base 302 is positioned below and configured to receive a bottom surface 304 of the container 324. The base 302 is designed as a cozy, partial enclosure, container, or receiver configured to receive the container 324. The base 302 includes a top surface 340 for receiving at least a portion of the bottom surface 304 of container 324.

Preferably, the walls of the container 324 are flexible to facilitate placement into and removal from the base 302. The container 324 conforms to the shape of the base 302 for proper fit, in one implementation, but does not lose its shape. In an embodiment, the top surface 334 of the base 302 is substantially horizontal, or parallel to the bottom external surface 344 of the base 302. In various implementations, the dimensions of the base 302 are in a range of approximately 12 to 16 inches wide×8 to 10 inches deep×3 to 7 inches high, preferably the dimensions of the base enclosure are 14 inches wide×10 inches deep×5 inches high.

The dimensions of the container 324 are preferably designed to be as small as possible, thereby improving portability, while still allowing for a container volume sufficient to contain all the requisite dialysate. Similarly, the base 302 is preferably designed to be as small while still being capable of receiving the bottom surface of the container 324.

Figure 3B:
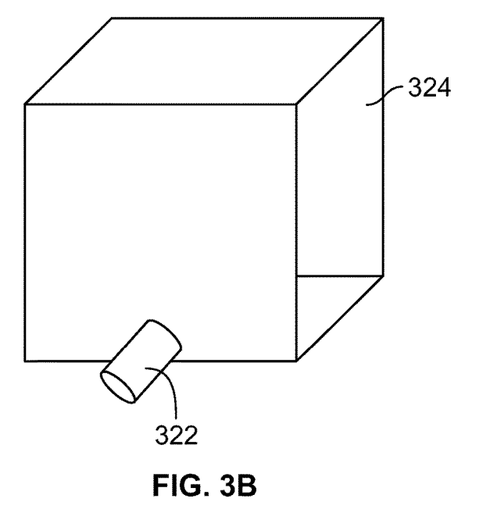
FIG. 3B illustrates an exemplary block diagram of a dialysate container with one tube functioning as both an inlet and outlet, in accordance with an implementation of the present specification.
Figure 3C:
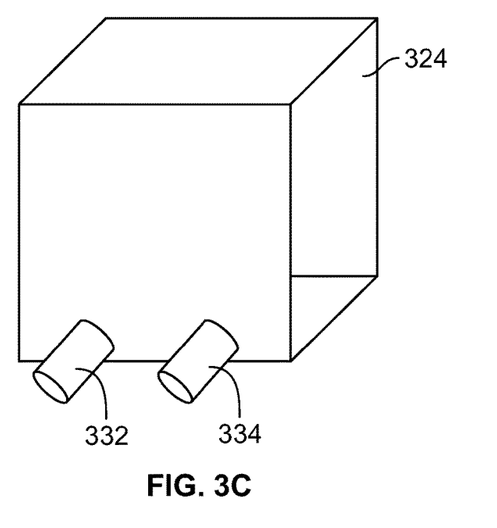
FIG. 3C illustrates an exemplary block diagram of a dialysate container with separate inlet and outlet tubes, in accordance with an implementation of the present specification.

In some implementations, the bottom surface 304 of the container 324 is substantially horizontal, or parallel to the bottom external surface 344 of the base 302, and not sloped or tilted. In some implementations, however, the bottom surface 304 of the container 324 is sloped or tilted to ensure complete removal of fluid from the container. Referring to FIGS. 3B and 3C, an outlet tube 322, 334 is placed proximate to the base of the container to ensure complete removal of fluid from the container, as further described below. The outlet tube 322, 334 is in fluid communication with the dialysis system via a tubing that connects the outlet tube 322, 334 to a disposable manifold housed within the dialysis system for filtration.

In one implementation, the height from the bottom of the container 324 where the outlet tube(s) or port(s) is placed ranges from ¼ to ½ inch. One of ordinary skill in the art would appreciate that if the outlet tube or port is placed too high from the bottom of the container 324, it will lead to a fluid residue in the container 324, even if the base of the container 324 is tilted. In an implementation, fluid is drawn from the container 324 by the pump action of the pumping unit of the dialysis system.

FIGS. 3B and 3C illustrate block diagrams of dialysate containers having straight (non-tilted) internal and external bottom surfaces, in accordance with some implementations of the present specification. Referring to FIG. 3B, there is one tube 322 in fluid communication with the internal volume of the container 324, which can function as an inlet or outlet, depending on the stage of treatment. In another implementation, referring to FIG. 3C, there are two tubes 332, 334 in fluid communication with the internal volume of the container 324, with a first tube 332 acting as an inlet and a second tube 334 acting as an outlet. In this case, fluid is returned to the container 324 after treatment and is re-circulated through the system.

Figure 3D:
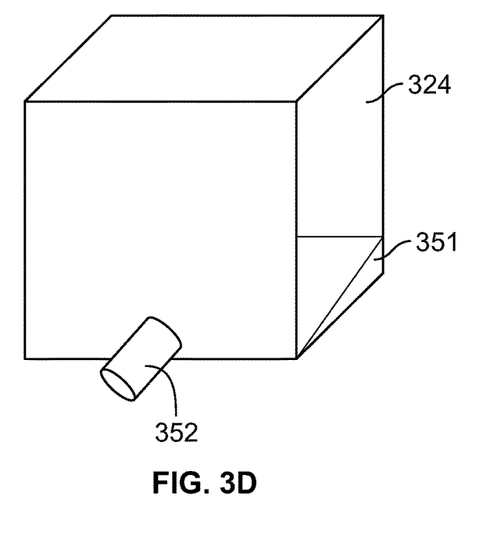
FIG. 3D illustrates an exemplary block diagram of a dialysate container with one tube functioning as both an inlet and outlet and a sloped internal bottom surface, in accordance with an implementation of the present specification.
Figure 3E:
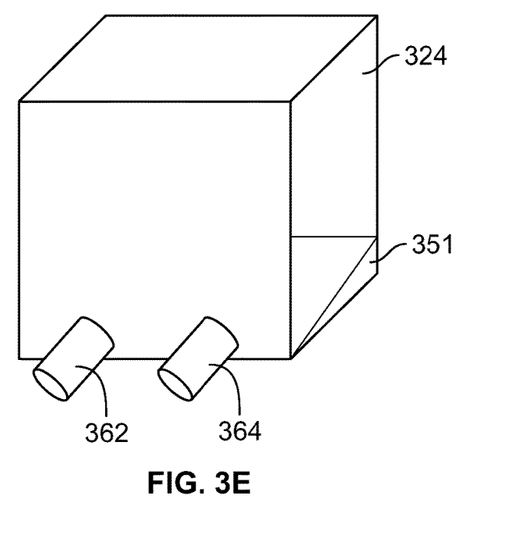
FIG. 3E illustrates an exemplary block diagram of a dialysate container with separate inlet and outlet tubes and a sloped internal bottom surface, in accordance with an implementation of the present specification.

In an implementation, the bottom 351 of the container 324 is internally sloped to allow for greater fluid removal. The angle of the slope or tilt of the internal bottom surface 351 of the container 324 ranges from 0.1 degrees to 50 degrees relative to a substantially horizontal surface.

FIGS. 3D and 3E illustrate block diagrams of containers 324 having internally sloped bottom "floors" 351, in accordance with some implementations of the present specification. Referring to FIG. 3D, one tube 352 is in fluid communication with the internal volume of the container 324 and extends out from the container 324 to thereby function as an inlet or outlet, depending on the stage of treatment. In another implementation, referring to FIG. 3E, there are two tubes 362, 364 in fluid communication with the internal volume of the container 324 and extending out from the container 360, with a first tube 362 configured as an inlet and a second tube 364 configured as an outlet. In this case, fluid may be returned to the container 324 after treatment and is re-circulated. As shown, the container 324 includes an internal sloped bottom floor 351 to direct fluid to the tubes 352, 364 respectively. The external bottom surface of the container may or may not reflect the tilt, or slope, of the internally sloped surface 351.

In one implementation, the height from the bottom of the container 324 where the outlet tube(s) or port(s) is placed ranges from ¼ to ½ inch. In an embodiment, a placement at ¼ inch or lower may represent the lowest point at which the outlet tube is positioned proximate to a sloped internal base surface and opposite from the highest point of said sloped internal base surface, wherein the highest point may be represented by a placement of ¼ to ½ inch proximate to said sloped internal base surface. One of ordinary skill in the art would appreciate that if the outlet tube or port is placed too high from the bottom of the container 324, it will lead to a fluid residue in the container 324, even if the base of the container 324 is tilted. In an implementation, fluid is drawn from the container 324 by the pump action of the pumping unit of the dialysis system.

Referring back to FIG. 3A, the base 302 comprises a weighing mechanism 308, such as a scale, for measuring the weight of the container 324 when water and/or compositions are placed into the container 324. The base 302 further optionally includes a battery 310 for power and a wireless transmitter 312 for wirelessly connecting to the dialysis machine for conveying the weight, conductivity and/or temperature of the dialysate solution to the dialysis machine without requiring a physical data connection to the dialysis machine. In another, less preferred implementation, the base 302 may be remote from, yet wired to, the dialysis machine to receive power and to transmit data.

Figure 5:
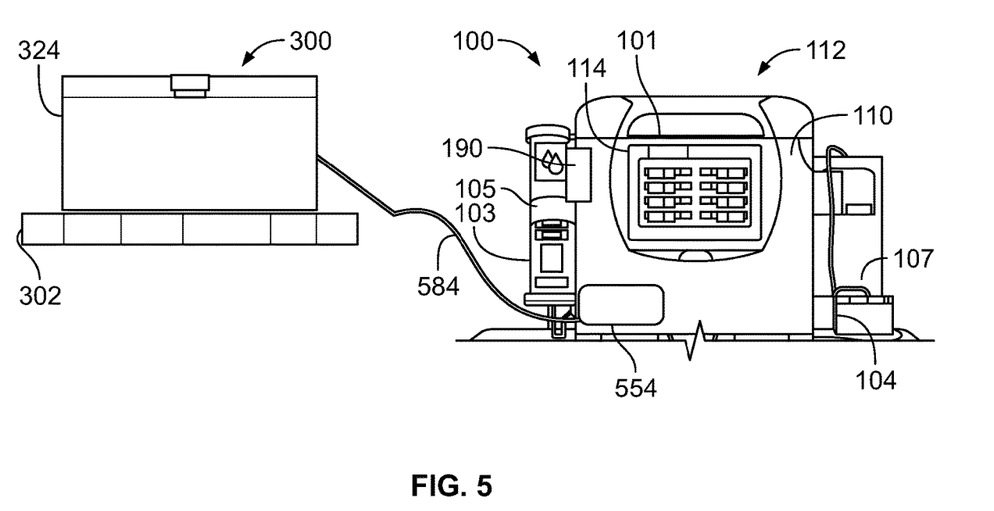
FIG. 5 illustrates an in-line heating element, in accordance with an implementation of the present specification.

In a preferred implementation, the container 324 is in fluid communication with an in-line heating mechanism, thereby enabling fluid to be heated as it flows through a pipe and without statically storing fluid for heating. Thus, the required dialysate may be heated to a desired temperature as it circulates through the dialysis system, without first having to wait for the dialysate to be heated in a reservoir. Referring to FIG. 5, in an implementation, the in-line heating mechanism 554 is a resistive or inductive heating element that is positioned longitudinally along, and in temperature communication with, a fluid pathway 584 extending from the container 324 to and/or through a manifold positioned within the dialysis system 100. The resistive heating element may comprise a plurality of wires that are in electrical communication with a controller configured to adjustably deliver electricity to the wires and, to generate heat when current is applied thereto, thereby increasing the temperature of proximate structures (e.g., including the fluid pathway 584). The inductive heating element may comprise a ferromagnetic material positioned on or cylindrically around the fluid pathway and an inductor sleeve cylindrically positioned around the ferromagnetic material. The inductor sleeve is in electrical communication with a controller configured to adjustably deliver electricity to the sleeve such that, when current is applied thereto, a magnetic field is created in the sleeve causing the nearby ferromagnetic material to heat up, thereby increasing the temperature of proximate structures (e.g., the fluid pathway 584) as well. Preferably, the heating element 554 is located in a pump unit relatively close to the blood filter of the dialysis system so that a minimum of heat energy is lost as the fluid moves through the heating element 554 to the required portions of the dialysis circuit.

In an alternative implementation, the base 302 may comprise an integrated heating element 376, for heating fluid in the container 324 to a predefined temperature. The heating element 376 may be an inductive heating element having a ferromagnetic base in physical communication with the container 324 and an inductor circuit positioned below the ferromagnetic base. The inductor circuit is in electrical communication with a controller in the base 302 configured to adjustably deliver electricity to the circuit such that, when current is applied thereto, a magnetic field is created in the circuit causing the nearby ferromagnetic base to heat up, thereby causing proximate structures, including the base of the container 324, to increase in temperature as well. The dialysate placed in the container 324 may, therefore, be pre-heated and primed to a desired temperature by using the base 302.

Referring back to FIG. 3A, in an implementation, a disposable sealable liner 306 is fitted within the container 324 of dialysate management system 300 above the bottom surface 304 of the container, as shown. The liner 306 may be made of a porous material and is designed to hold powdered compositions within a sealed compartment. When water is poured into the container 324, the water enters the porous liner 306 and the prescription is dissolved into the water producing the required dialysis solution. The liner 306 may include a fitting 307, positioned at the top of the liner, to which a prescription bag 309 containing the powdered compositions is attached such that, when water is poured into the container 324, the powdered compositions dissolve in the water producing the required dialysate. In an implementation, the fitting comprises a screw fitting. In another implementation, wherein the container does not include a liner, a fitting for affixing a prescription bag is included on the container itself. In another implementation, a prescription "pod" containing the powdered compositions in a porous substrate may be dropped into the container 324, which already is filled with a predefined quantity of water. The prescription pod then dissolves in the water producing the required dialysate. In another implementation, a second disposable, porous flexible container is fitted within the container 324 and configured to contain the powdered compositions, which eventually dissolve in the water that fills the container 324.

Where the container 324 includes a spout, a disposable liner may be folded and directed into the spout such that it fills the appropriate space. In one implementation, the liner adapts to the threads of the opening of the container, which is capped using a cap assembly. A fitting, such as a luer fitting with ¼ turn, is provided on the top of the cap. In one implementation, the liner is attached to another plastic component that holds a fitting. In an implementation, a portion of the liner is folded over the mouth of the container opening, and a plastic component is screwed onto a thread on the mouth of the opening, which fixes the liner in place. This arrangement is similar to a bottle cap or a bottle adapter, which is mated to the bottle by a screw mechanism.

It may be noted that since the liner is porous, it acts as a mesh or net and does not block or stop the flow of fluid to the outlet tube from the container. The liner is separate from the port opening, pick-up tube, or inlet/outlet tube at the bottom of the container. In some embodiments, the liner comprises notches such that a portion of the liner is sucked into an outlet tube and conforms to the shape of the tube, without blocking flow through the outlet tube. In some embodiments, the liner is configured as a plastic cage or net and acts as a porous ball on the outlet tube (a circular portion of the liner is pulled into the outlet tube) without blocking flow through the outlet tube.

In an implementation, the base 302 comprises a single, centrally located flexure assembly (not shown) for measuring the weight of the container 324 by using load cells and/or strain gauges. The flexure assembly may be mounted to the underside surface of the base 302 and include mounting plates, magnets, flexure rings, spacers, and a circuit board.

In another implementation, weight measurement is achieved using hall sensors and a circuit board integrated into the base 302. Hall sensors on the circuit board resistively sense changes in magnetic fields generated by the movement of the magnets for calculation of weight measurements. The circuit board and hall sensors are stationary and two sets of magnets, one above the board and another below the board, move vertically in relation to the board and fixed in relation to each other. The hall sensors sense the change in the magnetic field as the sets of magnets move when weight is applied to the base 302. The change in the magnetic field causes an output in voltage from the hall sensors. A processor on the circuit board processes the voltage output to determine the weight. Use of a flexure assembly with one axis of movement provides a scale system that is low cost, reliable, robust and easy to assemble and integrate into the base 302, as described in U.S. Pat. No. 9,157,786, which is incorporated herein by reference in its entirety. In implementations where the bottom of the container is sloped or tilted, the measured weight is mathematically adjusted using the angle of the tilt to compensate for weight not being measured on a level platform.

The base 302 preferably further comprises a conductivity measurement system 316 to measure the conductivity of the solution contained within the container 324. A conductivity coil, configured to generate a field and use changes in that field to measure conductivity, may be integrated into base 302 and positioned proximate the bottom surface of the container. Accordingly, when the container 324 is placed on base 302, it is heated and, because it is in contact with the conductivity coil, its conductivity is also monitored. In one implementation, the conductivity is measured using a conductivity coil, as described in U.S. Pat. No. 9,201,036, which is incorporated herein by reference in its entirety.

In an implementation, a non-invasive detection method based on ultrasonic time of flight (TOF) measurement is used to measure the conductivity and/or density of the solution contained in the container 324. The base 302 is provided with one or more ultrasonic sensors for non-invasive measuring of the conductivity and/or density of the fluid. The ultrasonic sensors also measure the level of the fluid in the container, providing differential redundancy with the weight measurement load cells to determine the amount of fluid in the container 324. The combination of load cells and ultrasonic sensors provides an accurate and reliable measurement of the weight and conductivity of the solution contained in the container 324. In embodiments, the accuracy of the load cells and/or ultrasonic sensors are within 5% of actual physical measurements of the conductivity, density, weight, and/or level of the fluid.

Figure 4A:
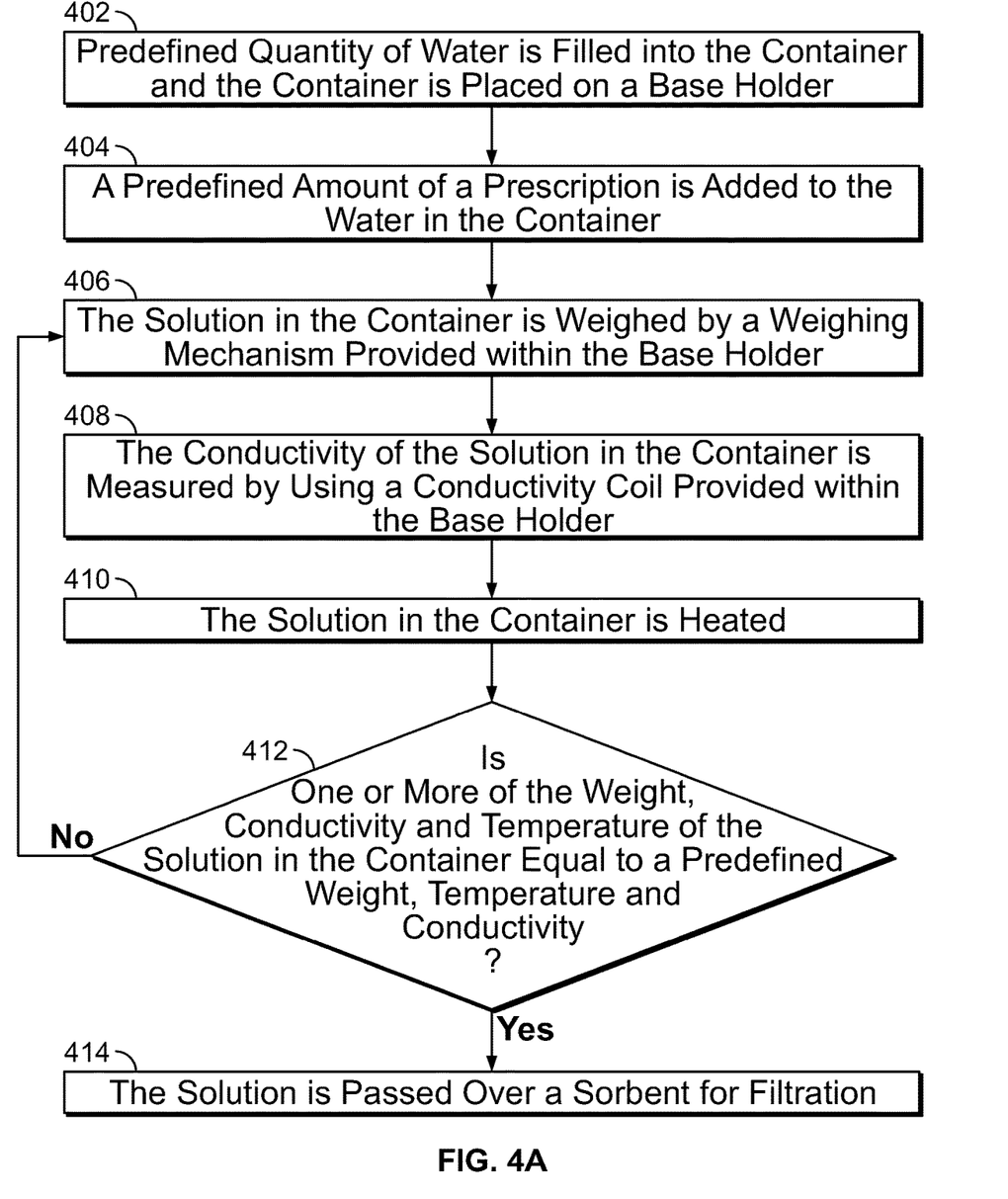
FIG. 4A is a flowchart illustrating exemplary steps of using a dialysate management system in accordance with one implementation of the present specification.

FIG. 4A is a flowchart illustrating exemplary steps of using a container 324 of the present specification. At step 402, the container 324 is filled with a predefined quantity of water and placed on a base 302. At step 404, a predefined amount of prescribed materials, in the form of powdered compositions, is added to the water in the container 324. The powdered compositions may be in a loose powder form, in the form of a prescription pod, or in the form of a disposable lining positioned within the container 324, such that when water is poured into the container 324, the water enters the liner and the powdered compositions dissolve in the water producing the required dialysate. In implementations, the predefined amount of prescribed materials or powdered compositions is dependent upon a physician's prescription for a particular user. Further the acceptable ranges of weight and conductivity are, in turn, dependent upon the nature of the user's prescription. In implementations, the controller unit is programmed in accordance with the user's prescription. In implementations, an acceptable weight range, in accordance with a user's prescription(s), is stored in an internal memory so that it can be compared to a measured weight. In implementations, an acceptable conductivity range, in accordance with a user's prescription(s), is stored in an internal memory so that it can be compared to a measured conductivity.

At step 406, the solution in the container 324 is weighed by one of the aforementioned weighing mechanisms integrated into the base 302. At step 408, the conductivity of the solution in the container 324 is measured using a conductivity coil provided within the base enclosure. At step 410, the solution in the container 324 is heated. In one implementation, the solution is heated using an in-line heating mechanism external to the base 302. This allows water or fluid to be heated as it flows through a fluid pathway, and does not require the fluid to be statically stored for heating. Thus, water is heated to a desired temperature as it circulates through the dialysis system. In another implementation, the solution in the container 324 may be heated by a heating element provided within the base 302.

At step 412, data regarding the weight, conductivity and/or temperature of the dialysate is transmitted from the base 302 to the controller positioned in the top unit 101 of dialysis system 100. Where an in-line heater is used external to the base 302, a temperature sensor positioned after the in-line heater is configured to measure the fluid temperature and transmit the requisite temperature data to the controller. The controller in the top unit 101 of dialysis system 100 determines if one or more of the weight, conductivity, and temperature of the solution in the container 324 is equal to, or falls within, a predefined weight, temperature, and conductivity range. If the weight, conductivity, and/or temperature do not equal or fall within predefined value ranges, an alarm is triggered requiring the container 324 to be weighed again (and water may be added or removed from the container), conductivity to be measured again, and heating to be repeated or continued until the desired values are met. If the weight, conductivity, and temperature equal or fall within predefined value ranges, at step 414, the dialysate solution is passed through a sorbent cartridge for filtration.

Figure 4B:
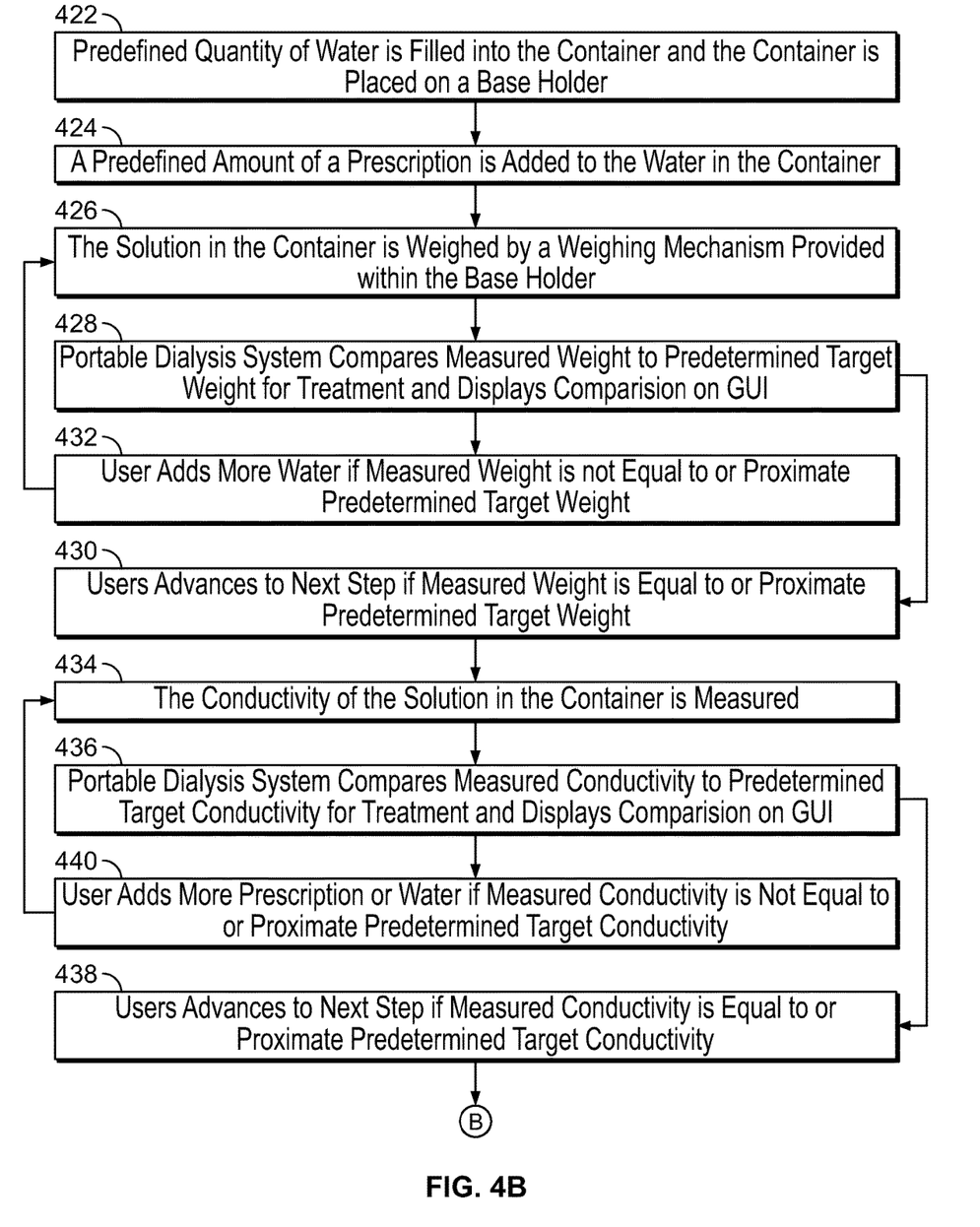
FIG. 4B is a flowchart illustrating exemplary steps of using a dialysate management system in accordance with another implementation of the present specification.

FIG. 4B is a flowchart illustrating exemplary steps of using the dialysate management system in accordance with another implementation of the present specification. At step 422, the container 324 is filled with a predefined quantity of water and placed on base 302. At step 424, a predefined amount of a prescribed powdered compositions is added to the water in the container 324. The powdered compositions may be in a loose powder form, the form of a prescription pod, or in the form of a disposable lining positioned within the container 324, such that when water is poured into the container 324, the water enters the liner, and the powdered compositions dissolve in the water producing the required dialysate. At step 426, the solution in the container 324 is weighed by one of the aforementioned weighing mechanisms provided within the base 302. At step 428, the base 302 transmits the weight data to the controller in the portable dialysis system and the controller compares the measured weight to a predetermined target weight and displays the comparison on a graphical user interface (GUI), where the GUI is located either on a visual display integrated into container 324 or base 302 or the portable dialysis system. The user then either adds more water or removes water if the measured weight is not equal to or proximate the predetermined target weight at step 432. If the measured weight is equal to or proximate the predetermined target weight, the user advances to the next step at step 430. In various implementations, a measured weight is considered sufficiently proximate if it falls within +/−10% of the predetermined target weight. If the user adds more water at step 432, then the solution is weighed again at step 426, and the process iterates accordingly.

At step 434, the conductivity of the solution in the container 324 is measured as described above using a conductivity coil integrated into the base 302 and the conductivity data is transmitted to the controller in the dialysis system. At step 436, the controller compares the measured conductivity to a predetermined target conductivity for treatment and displays the comparison on a graphical user interface (GUI), where the GUI is located either on a visual display integrated into container 324 or base 302 or the portable dialysis system. The user then either adds more powdered compositions or water if the measured conductivity is not equal to or proximate the predetermined target conductivity at step 440 or advances to the next step if the measured conductivity is equal to or proximate the predetermined target conductivity at step 438. In various implementations, a measured conductivity is considered proximate if it falls within +/−10% of the predetermined target conductivity. If the user adds more prescription or water at step 440, then the solution conductivity is measured again at step 434, and the process iterates accordingly.

At step 442, the solution in the container 324 is heated. In one implementation, the solution is heated using an external, in-line heating mechanism as described above. This allows water or fluid to be heated as it flows through a pipe or a container, and does not require the fluid to be stored for heating. Thus, water is heated to a desired temperature as it circulates through the dialysis system. In an implementation, the heating element is located in the controller portion of top unit 101 of the dialysis system 100 relatively close to the blood filter so that a minimum amount of heat energy is lost as the fluid moves from the heating element to the filter. In an alternate implementation, the solution in the container 324 may be heated by a heating element provided within the base 302.

At step 444, the temperature of the solution in the container 324 is measured by a temperature sensor. In an implementation, the temperature is measured by a temperature sensor installed in the base 302. In another implementation, the temperature of the solution may be measured by a temperature sensor positioned external to the container 324 or the base 302. Data from the temperature sensor is transmitted to the controller of the dialysis unit. At step 446, the controller compares the measured temperature to a predetermined target temperature for treatment and displays the comparison on a graphical user interface (GUI), where the GUI is located either on a visual display integrated into container 324 or base 302 or the portable dialysis system. The user then either allows the solution to continue to heat or cool if the measured temperature is not equal to or proximate the predetermined target temperature at step 450 or advances to the next step if the measured temperature is equal to or proximate the predetermined target temperature at step 448. In various implementations, a measured temperature is considered proximate if it falls within +/−10% of the predetermined target temperature. If the user allows the solution to continue to heat or cool at step 450, then the solution temperature is measured again at step 444, and the process iterates accordingly. At step 452, the solution is passed through a sorbent cartridge for filtration if the weight, conductivity, and temperature of the solution in the container are equal to or proximate a predefined weight, conductivity, and temperature as determined by the dialysis system.

In implementations, retrofitting any conventional dialysis system with the novel disclosed dialysate management system and removing or not using the conventional reservoir system will result in a decrease of at least 10%, preferably upwards or 40% and any increment therein, of priming time associated with the generation of filtered, heated dialysate from a dialysate mixture.

In an implementation, the measured values of weight, conductivity, and temperature are wirelessly transmitted to the dialysis machine, which verifies the values and sends the confirmation back to the base 302. In another implementation, the measured values are communicated using a wired connection between the container 324/base 302 and the dialysis system. In some implementations, the wired connection functions as a backup line if the wireless connection fails and comprises a USB, serial, or parallel connection. In yet another implementation, the measured values are manually inputted to the dialysis system using a user interface. In some implementations, the interface is located on the container 324 and/or base 302. In other implementations, the interface is the same interface that is located on the dialysis system. In various implementations, the user interface, either on the container 324, the base 302 or top unit 101 of the dialysis system 100, display indications to the user that the weight or conductivity of the container contents do not match predetermined values and to add more prescription or fluid, or the temperature of the fluid does not match a predetermined value, and that further heating is required. In some implementations, the indications include visual and audible indications, including, but not limited to, digital displays, colored icons, and audio alarms.

In some implementations, the container 324 is equipped with indicator lights and/or a display panel, which indicates power and measured readings. In another implementation, the user interface of the dialysis system (shown as 114 and 214 in FIG. 1 and FIG. 2) is used to display the measured readings and status values from the container 324 and base 302. In an implementation, power is supplied to the container 324 and base 302 using a rechargeable battery that can be charged by the main power unit of the dialysis system. In other implementations, power is supplied to the container/enclosure via a USB cable or power cord. The above examples are merely illustrative of the many applications of the reservoir bag of the present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A dialysate generation system for generating a dialysate fluid external to a dialysis machine, wherein the dialysis machine is configured to receive and use the dialysate fluid to conduct a dialysis treatment session, comprising:
a container defined by a plurality of molded plastic walls forming a polygonal housing with a flat external bottom surface, positioned external to the dialysis machine and configured to hold dialysate fluid, wherein the container comprises an internal base surface that, relative to a substantially horizontal surface, has a slope in a range of 0.1 degrees to 50 degrees and an outlet tube and wherein the internal base surface is adapted to directly contact the dialysate fluid and is fixedly coupled to the substantially horizontal surface;
a base enclosure external to the dialysis machine having a flat top surface and configured to detachably receive the bottom surface of the container, wherein the base enclosure comprises:
   a first scale in physical communication with the bottom surface of the container and configured to weigh the dialysate fluid positioned within the container; and
   a conductivity sensor positioned proximate the bottom surface of the container and configured to measure a conductivity of the dialysate fluid in the container;
a fluid pathway connected to the outlet tube and extending from the container to the dialysis machine; and
a heating element positioned external to the base enclosure and configured to heat the dialysate fluid as the dialysate fluid passes through the fluid pathway, wherein the heating element comprises a resistive or an inductive heating element positioned cylindrically along the fluid pathway, longitudinally along the fluid pathway, and in temperature communication with the fluid pathway.

2. The dialysate generation system of claim 1, wherein the container further comprises powdered compositions enclosed within a disposable porous material.

3. The dialysate generation system of claim 1, wherein the outlet tube is positioned proximate to a lowest point of the sloped internal base surface and opposite from the highest point of the sloped internal base surface.

4. The dialysate generation system of claim 3, wherein the outlet tube is positioned at a height ranging from ¼ to ½ inch from an external bottom surface of the container.

5. The dialysate generation system of claim 1, further comprising a wireless transmitter configured to wirelessly transmit at least one of weight data and conductivity data to a controller in a dialysis machine, wherein the dialysis machine is in electronic communication with the dialysate generation system.

6. The dialysate generation system of claim 1, wherein the first scale comprises a flexure assembly.

7. The dialysate generation system of claim 6, wherein the flexure assembly comprises at least one of a load cell or strain gauge.

8. The dialysate generation system of claim 1, wherein the conductivity sensor comprises a conductivity coil.

9. The dialysate generation system of claim 1, wherein the conductivity sensor comprises ultrasonic sensors.

10. A dialysis system, comprising:
a dialysis machine comprising:
   a dialysate fluid circuit having a fluid pathway and a blood fluid circuit;
   a dialyzer in fluid communication with the dialysate fluid circuit and blood fluid circuit;
   a sorbent cartridge in fluid communication with said dialysate fluid circuit;
   a plurality of pumps in physical communication with the dialysate fluid circuit and the blood fluid circuit; and
   a processing unit for controlling an operation of the plurality of pumps; and
a dialysate generation system physically separate from the dialysis machine, the dialysate generation system comprising:
   a container defined by a plurality of molded plastic walls forming a polygonal housing with a flat external bottom surface and configured to hold dialysate fluid, wherein the container comprises an outlet tube that is in fluid communication with the fluid pathway in the dialysate fluid circuit, a bottom portion, and an internal base surface that, relative to a substantially horizontal surface, has a slope in a range of 0.1 degrees to 50 degrees and wherein the internal base surface is adapted to directly contact the dialysate fluid and is fixedly coupled to the substantially horizontal surface, and
   a base enclosure configured to detachably receive the bottom surface of the container, wherein the base enclosure comprises:
      a scale in physical communication with the bottom surface of the container and configured to weigh the dialysate fluid positioned within the container; and
      a conductivity sensor configured to measure a conductivity of the dialysate fluid in the container; and
   a heated fluid pathway connected to the outlet tube and extending from the container to the dialysis machine comprising a heating element configured to heat the dialysate fluid as the dialysate fluid passes through the fluid pathway, wherein the heating element comprises a resistive or an inductive heating element positioned cylindrically along the fluid pathway, longitudinally along the fluid pathway, and in temperature communication with the fluid pathway.

11. The dialysate system of claim 10, wherein the outlet tube is positioned proximate to a lowest point of the sloped internal base surface and opposite from the highest point of the sloped internal base surface.

12. The dialysate system of claim 11, wherein said outlet tube is positioned at a height ranging from ¼ to ½ inch from an external bottom surface of the container.

13. The dialysate system of claim 10, wherein the container further comprises powdered compositions enclosed within a disposable porous material.

14. The dialysate system of claim 10, further comprising a wireless transmitter configured to wirelessly transmit at least one of weight data and conductivity data to the processing unit.

15. A method of generating dialysate using a dialysate generation system, wherein the dialysate generation system is physically separate from a dialysis controller unit and wherein the dialysate generation system comprises a container configured to hold fluid, wherein the container comprises an external flat bottom surface, an internal base surface that, relative to a substantially horizontal surface, has a slope in a range of 0.1 degrees to 50 degrees wherein the internal base surface is adapted to directly contact the dialysate fluid and is fixedly coupled to the substantially horizontal surface, and an outlet tube that is in fluid communication with a fluid pathway positioned between the dialysate generation system and the dialysis controller unit, wherein the dialysate generation system further comprises a base enclosure configured to detachably receive the bottom surface-of the container, and wherein the base enclosure comprises:
   a scale in physical communication with the bottom surface of the container and configured to weigh the fluid positioned within the container and
   a conductivity sensor positioned proximate the bottom surface of the container and configured to measure a conductivity of the fluid in the container, the method comprising:
filling a predefined quantity of water into the container;
placing the container in the base enclosure;

adding at least one powdered composition to the water in the container to create dialysate fluid;

weighing the dialysate fluid in the container using the scale;

measuring a conductivity of the dialysate fluid in the container using the conductivity sensor;

determining if the weight and conductivity of the fluid in the container falls within a range of acceptable values for weight and conductivity;

causing the dialysate fluid to flow from the outlet tube to the fluid pathway positioned between the dialysate generation system and the dialysis controller unit;

heating the dialysate fluid in the fluid pathway using an in-line heating element, wherein the in-line heating element comprises a resistive or an inductive heating element positioned cylindrically along the fluid pathway, longitudinally along the fluid pathway, and in temperature communication with the fluid pathway; and passing the dialysate fluid over a sorbent for filtration.

16. The method of claim 15, further comprising adjusting a measured weight of the dialysate fluid to account for an unequal distribution of dialysate fluid across the internal base surface due to the slope in a range of 0.1 degrees to 50 degrees.

* * * * *